(12) United States Patent
Wink et al.

(10) Patent No.: US 9,012,647 B2
(45) Date of Patent: Apr. 21, 2015

(54) NITROXIDE MODIFIED NON-STEROIDAL ANTI-INFLAMMATORY COMPOUNDS AND USES THEREOF IN THE TREATMENT AND PREVENTION OF DISEASES OR DISORDERS

(75) Inventors: David A. Wink, Hagerstown, MD (US); Wilmarie Flores-Santana, Montgomery Village, MD (US); S. Bruce King, Walnut Cove, NC (US); Murali Krishna Cherukuri, Gaithersburg, MD (US); James B. Mitchell, Damascus, MD (US)

(73) Assignees: The United States of America, as Represented by the Secretary, Department of Health and Human Services, Washington, DC (US); Wake Forest University, Winston-Salem, NC (US)

( * ) Notice: Subject to any disclaimer, the term of this patent is extended or adjusted under 35 U.S.C. 154(b) by 0 days.

(21) Appl. No.: 13/440,092

(22) Filed: Apr. 5, 2012

(65) Prior Publication Data
US 2012/0263650 A1    Oct. 18, 2012

Related U.S. Application Data

(60) Provisional application No. 61/472,770, filed on Apr. 7, 2011.

(51) Int. Cl.
| | | |
|---|---|---|
| *A61K 31/445* | (2006.01) | |
| *C07D 211/00* | (2006.01) | |
| *C07D 401/12* | (2006.01) | |
| *C07D 211/94* | (2006.01) | |
| *A61K 47/48* | (2006.01) | |

(52) U.S. Cl.
CPC ............ *C07D 401/12* (2013.01); *C07D 211/94* (2013.01); *A61K 47/48061* (2013.01)

(58) Field of Classification Search
None
See application file for complete search history.

(56) References Cited

U.S. PATENT DOCUMENTS

| | | |
|---|---|---|
| 4,863,457 A | 9/1989 | Lee |
| 5,378,475 A | 1/1995 | Smith et al. |
| 5,443,505 A | 8/1995 | Wong et al. |
| 8,383,648 B2 * | 2/2013 | Matier et al. .................. 514/315 |
| 2005/0131025 A1 | 6/2005 | Matier et al. |
| 2008/0318907 A1 | 12/2008 | Ba et al. |

FOREIGN PATENT DOCUMENTS

WO     WO 03/096991 A2     11/2003

OTHER PUBLICATIONS

CAPLUS 1997:561656.*
CAPLUS 1987:32779.*
CAPLUS 1994:270121.*
CAPLUS 1988:221563.*
CAPLUS 1979:508525.*
Berge et al., "Pharmaceutical Salts," *J. Pharm. Sci.*, 66 (1), 1-19 (1977).
Choy et al., "Enhancing radiotherapy with cyclooxygenase-2 enzyme inhibitors: a rational advance?," *J. Natl. Cancer Inst.*, 95 (19), 1440-1452 (2003).
Davies et al., "Pharmacological protection of NSAID-induced intestinal permeability in the rat: effect of tempo and metronidazole as potential free radical scavengers," *Hum. Exp. Toxicol.*, 16 (7), 345-349 (1997).
Flores-Santana et al., "Nitroxide derivatives of non-steroidal antiinflammatory drugs exert anti-inflammatory and superoxide dismutase scavenging properties in A459 cells," *British J. Pharmacol.*, 165, 1058-1067 (2012).
Flores-Santana et al., Modified Non-Steroidal Anti-Inflammatory Drug with SOD Mimetic Nitroxide, poster and abstract presented at the EPR meeting, held May 2, 2010.
Flores-Santana et al., Modified Non-Steroidal Anti-Inflammatory Drug with the SOD mimetic Nitroxide, abstract presented at the NCI Postdoctoral retreat, held Mar. 17-19, 2010.
Hahn et al., "Tempol, a stable free radical, is a novel murine radiation protector," *Cancer Res.*, 52 (7), 1750-1753 (1992).
Krishna et al., "Do nitroxide antioxidants act as scavengers of O2—. or as SOD mimics?," *J. Biol. Chem.*, 271 (42), 26026-26031 (1996).
Krishna et al., "Oxoammonium cation intermediate in the nitroxide-catalyzed dismutation of superoxide," *Proc. Natl. Acad. Sci.*, 89 (12), 5537-5541 (1992).

(Continued)

*Primary Examiner* — Heidi Reese
(74) *Attorney, Agent, or Firm* — Leydig, Voit & Mayer

(57) ABSTRACT

Disclosed are nitroxide modified NSAID compounds of the formula (I) or a pharmaceutically acceptable salt or enantiomer thereof:

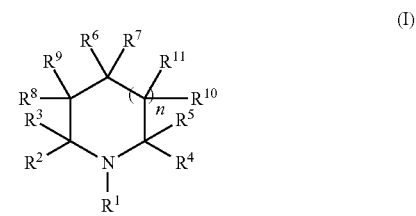

(I)

Figure 1:
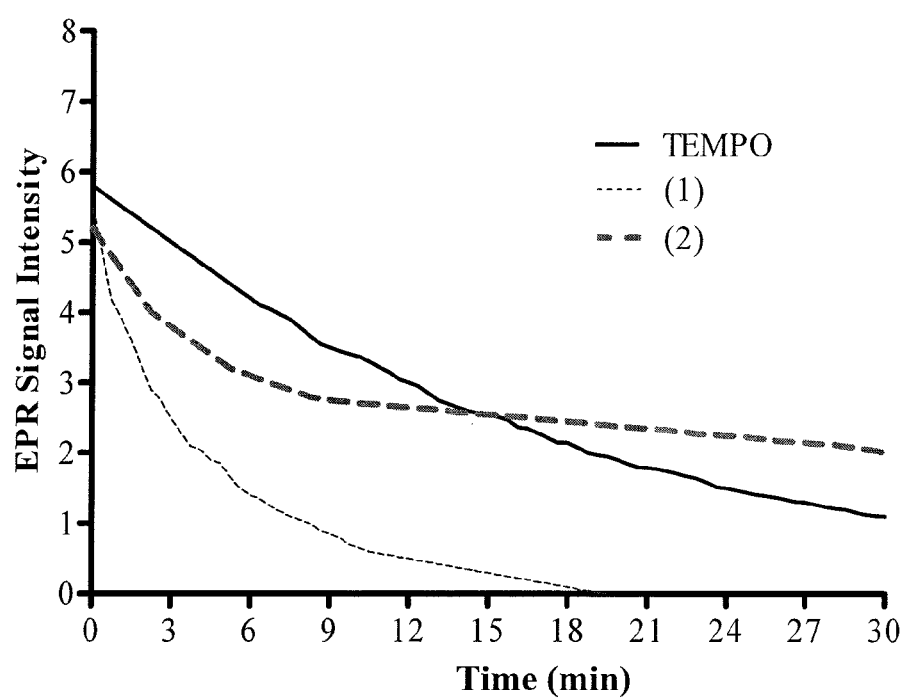

in which $R^1$, $R^2$, $R^3$, $R^4$, $R^5$, $R^6$, $R^7$, $R^8$, $R^9$, $R^{10}$, $R^{11}$, and n are defined herein and pharmaceutical compositions thereof. Further disclosed is a method of treating or preventing various disorders, such as inflammation, cancer, diabetes, a cardiovascular disorder, weight gain, polyps, and/or chronic pain, in a patient comprising administering an effective amount of a compound or pharmaceutically acceptable salt or enantiomer of formula (I). A method of imaging the compound or pharmaceutically acceptable salt or enantiomer of formula (I) in the body of the animal is also provided.

8 Claims, 5 Drawing Sheets

(56) References Cited

OTHER PUBLICATIONS

Liao et al., "A phase I clinical trial of thoracic radiotherapy and concurrent celecoxib for patients with unfavorable performance status inoperable/unresectable non-small cell lung cancer," *Clin. Cancer Res.*, 11 (9), 3342-3348 (2005).

Martel-Pelletier et al., "Therapeutic role of dual inhibitors of 5-LOX and COX, selective and non-selective non-steroidal anti-inflammatory drugs," *Ann. Rheum. Dis.*, 62 (6), 501-509 (2003).

Monti et al., "Protective effect of the nitroxide tempol against the cardiotoxicity of adriamycin," *Free Radic Biol. Med.*, 21 (4), 463-470 (1996).

Rachmilewitz et al., "A novel antiulcerogenic stable radical prevents gastric mucosal lesions in rats," *Gut*, 35 (9), 1181-1188 (1994).

Samuni et al., "Factors Influencing Nitroxide Reduction and Cytotoxicity In Vitro," *Antioxid. Redox. Signal*, 6 (3), 587-595 (2004).

Samuni et al., "Superoxide reaction with nitroxides," *Free Rad. Res. Comms.*, 9 (3-6), 241-249 (1990).

Swartz et al., "Cellular metabolism of water-soluble nitroxides: effect on rate of reduction of cell/nitroxide ratio, oxygen concentrations and permeability of nitroxides," *Biochim Biophys Acta*, 888 (1), 82-90 (1986).

Trnka et al., "Antioxidant properties of MitoTEMPOL and its hydroxylamine," *Free Radic Res.*, 43 (1), 4-12 (2009).

Utsumi et al., "Noninvasive mapping of reactive oxygen species by in vivo electron spin resonance spectroscopy in indomethacin-induced gastric ulcers in rats," *J. Pharmacol. Exp. Ther.*, 317 (1), 228-235 (2006).

Velazquez et al., "Novel nonsteroidal antiinflammatory drugs possessing a nitric oxide donor diazen-1-ium-1,2-diolate moiety: design, synthesis, biological evaluation, and nitric oxide release studies," *J. Med. Chem.*, 48 (12), 4061-4067 (2005).

Wasserman et al., "Semi-synthetic analogs of cytochrome c. Substitutions for methionine at position 80," *Biochim. Biophys. Acta*, 623 (2), 457-460 (1980).

Winter et al., "Carrageenin-induced edema in hind paw of the rat as an assay for antiiflammatory drugs," *Proc. Soc. Exp. Biol. Med.*, 111, 544-547 (1962).

Yoshimura et al., "Inhibitory effect of flavonoids on the efflux of N-acetyl 5-aminosalicylic acid intracellularly formed in Caco-2 cells," *J. Biomed. Biotechnol.*, 467-489 (2009).

\* cited by examiner

NITROXIDE MODIFIED NON-STEROIDAL ANTI-INFLAMMATORY COMPOUNDS AND USES THEREOF IN THE TREATMENT AND PREVENTION OF DISEASES OR DISORDERS

CROSS-REFERENCE TO RELATED APPLICATION

This patent application claims the benefit of U.S. Provisional Patent Application No. 61/472,770, filed Apr. 7, 2011, which is incorporated by reference in its entirety herein.

BACKGROUND OF THE INVENTION

Non-steroidal anti-inflammatory drugs (NSAID) have been used to treat numerous inflammatory conditions. Conditions such as arthritis and cancer require that NSAIDs be taken chronically for extended periods of time. For example, aspirin and cyclooxygenase-2 (COX-2) specific drugs such as, e.g., CELEBREX® (celecoxib capsules) and VIOXX® (rofecoxib) have been shown to reduce some types of cancer by over 50% when taken over a long period of time. Though there are beneficial effects, long-term use even with COX-2 selective agents may have problematic side effects leading to, e.g., gut ulceration and/or thrombosis. Attempts have been made to develop NSAIDs with reduced gut toxicity and/or thrombosis. However, there exists an unmet need for additional NSAIDs having reduced gut toxicity and/or thrombosis.

BRIEF SUMMARY OF THE INVENTION

The invention provides compounds comprising one or more NSAID moieties and at least one nitroxide moiety, compositions comprising such compounds, methods of use of such compounds in the treatment or prevention of disorders such as cancer, and methods of use of such compounds in the imaging of tissues and organs in the body of an animal. The compounds of the invention have one or more advantages: little or reduced gut toxicity, little or reduced thrombosis, and antioxidant properties. In an embodiment, the compounds of the invention are redox modified NSAIDs. In accordance with an embodiment, the compounds of the invention are redox modified NSAIDs having anticancer activity and superoxide dismutase (SOD) mimetic activity.

BRIEF DESCRIPTION OF THE SEVERAL VIEWS OF THE DRAWING(S)

FIG. 1 is a graph showing rapid uptake of nitroxide by A549 cells as shown by electron paramagnetic resonance (EPR) signal intensity for each of TEMPO (solid line), compound (1) (TEMPO-aspirin) (dotted line), and compound (2) (TEMPO-indomethacin) (dashed line) over time (min.). The decay curve shows the reduction of the TEMPO to TEMPO-H. X-band EPR: Scan Range $10 \times 10^1$ G, Time constant: 0.128, Mod. Ampl: $0.5 \times 10^1$ H, Field Set: 3360 G; Cell density $2.2 \times 10^7$ cells ml$^{-1}$, 37° C.

Figure 2:
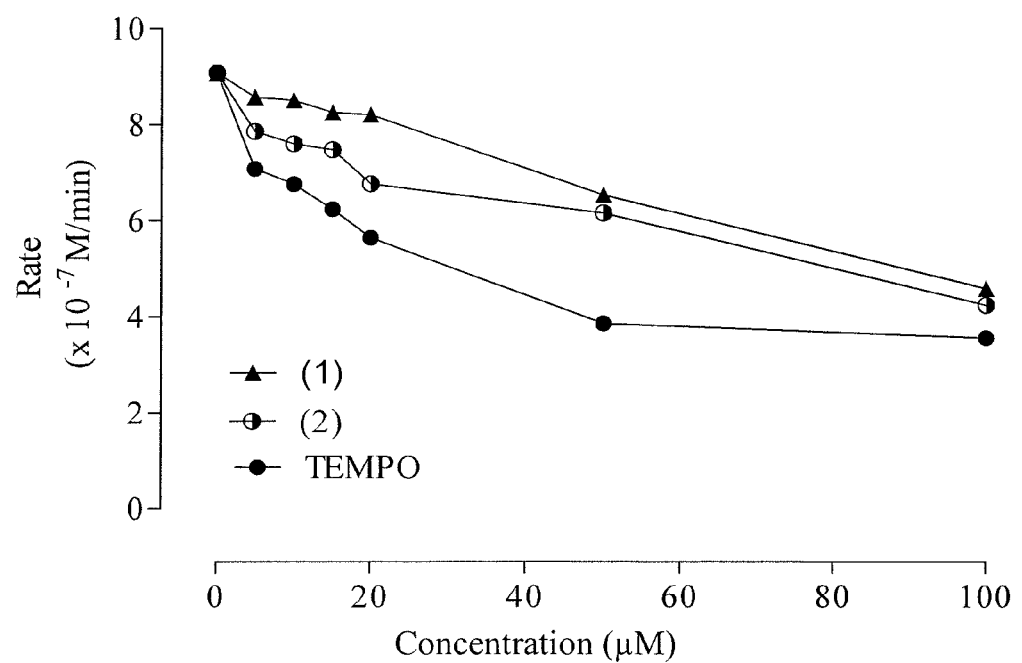

FIG. 2 is a graph showing initial reduction rates ($\times 10^{-7}$ M/min) of ferricytochrome c in the presence of various concentrations (μM) of compound (1) (TEMPO-aspirin) (▲), compound (2) (TEMPO-indomethacin) (half-shaded circle), and TEMPO (●) as monitored by a UV/Vis spectrophotometer at 550 nm.

Figure 3:
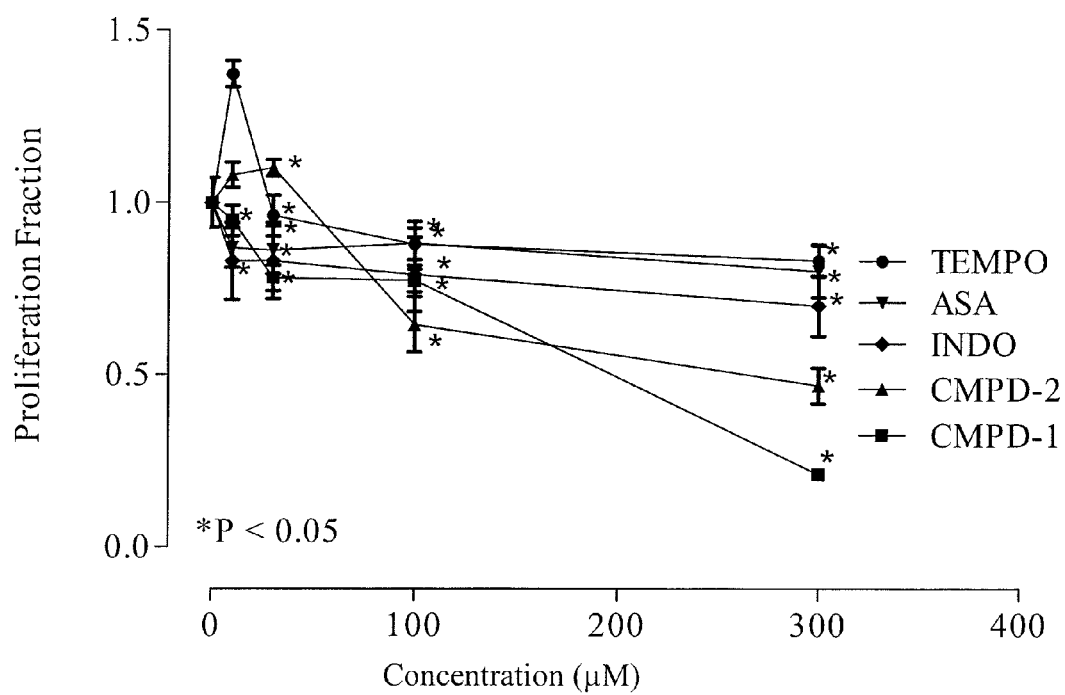

FIG. 3 is a graph showing the proliferation fraction of A549 cells after treatment with various concentrations of 2,2,6,6-tetramethyl-1-piperidinyloxy (TEMPO) (●), acetyl salicylic acid (ASA) (▼), indomethacin (INDO) (♦), TEMPO-aspirin (CMPD-1) (■), or TEMPO-indomethacin (CMPD-2) (▲). Values are mean of 18 determinations. Absorbance was measured at 590 nm with a cell density of $5 \times 10^3$ cell/well. Values (Proliferation Fraction) were obtained by dividing the average of the measurements of each treatment by the average of control. *indicates P values <0.05, t-test.

Figure 4:
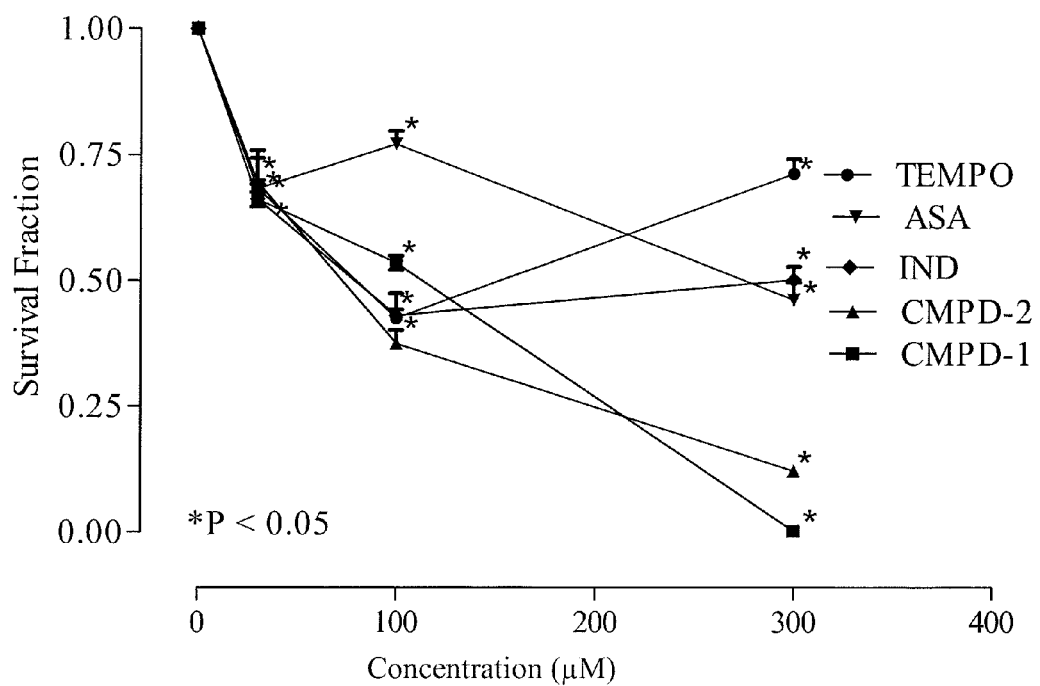

FIG. 4 is a graph showing the survival fraction of A549 cells after treatment with various concentrations of TEMPO (●), ASA (▼), INDO (♦), TEMPO-aspirin (CMPD-1) (■), or TEMPO-indomethacin (CMPD-2) (▲). Colonies were counted after 2 weeks of seeding the cells. Values are the mean values of triplicate experiments, P<0.05, t-test.

Figure 5:
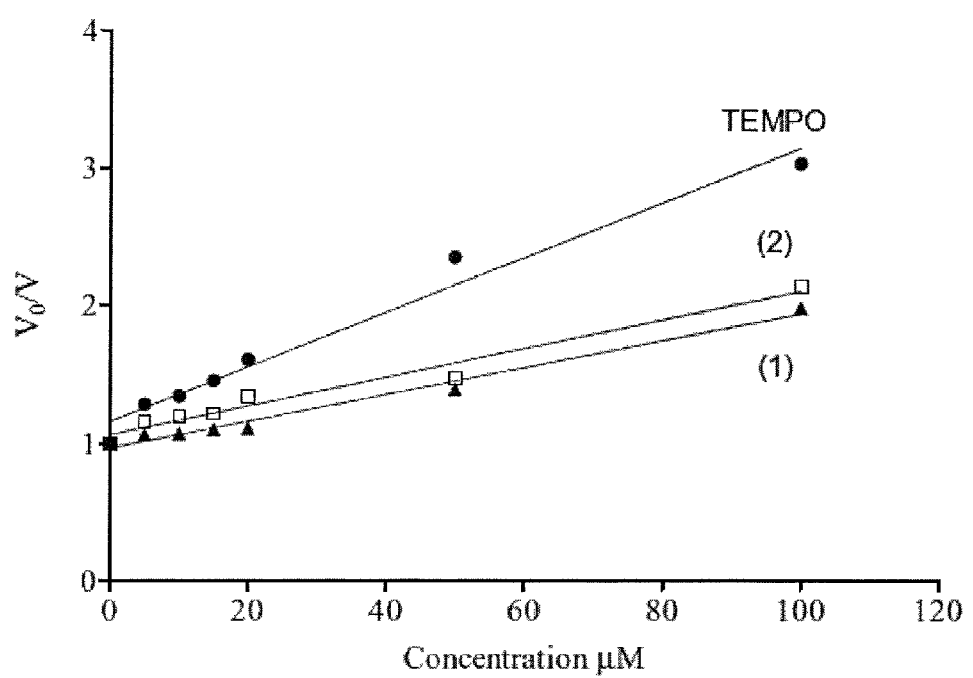

FIG. 5 is a graph showing the reduction rate and determination of the rate constant of nitroxide. Superoxide generation was measured by ferricytochrome c III generation in the presence (V) and absence (V$_0$) of nitroxide in varying concentrations (5-100 μM); (•) TEMPO, (▲) (TEMPO-aspirin, (1)), and (□) (TEMPO-indomethacin, (2)). The data were plotted according to the equation: $V_0/V = 1 + (k_{nitroxide/scavenger} \times [\text{nitroxide}])/(k_{cyt} \times [\text{cyt c}])$ as described in Samuni et al., *Free Radic Res. Commun.*, 9: 241-49 1990. The data points were fitted using a linear regression analysis, which gave correlation coefficients of 0.97, 0.98, and 0.97 for TEMPO and compounds TEMPO-aspirin and TEMPO-indomethacin, respectively.

DETAILED DESCRIPTION OF THE INVENTION

In accordance with an embodiment, the invention provides a compound of formula I

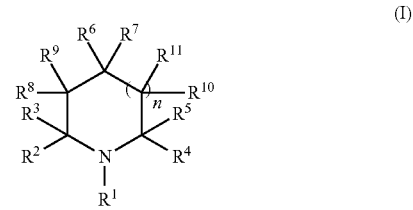

(I)

wherein

R$^1$ is selected from the group consisting of OH, OZ, O, and =O, wherein Z is selected from the group consisting of C$_{1-12}$ alkyl, C$_{2-12}$ alkenyl, C$_{3-8}$ cycloalkyl, C$_{3-8}$ heterocycloalkyl, and C$_{6-30}$ aryl;

R$^2$, R$^3$, R$^4$, and R$^5$ are the same or different and are selected from the group consisting of hydrogen, C$_{1-12}$ alkyl, C$_{2-12}$ alkenyl, and C$_{2-12}$ alkynyl;

R$^6$ and R$^7$ are the same or different and are selected from the group consisting of hydrogen, halogen, hydroxyl, mercapto, cyano, isothiocyanato (—NCS), C$_{1-12}$ alkyl, C$_{2-12}$ alkenyl, C$_{3-8}$ cycloalkyl, C$_{3-8}$ heterocycloalkyl, C$_{6-30}$ aryl, C$_{1-12}$ alkoxy, C$_{1-12}$ alkylthio, amino, alkylamino, dialkylamino, arylamino, diarylamino, alkylsulfonyloxy, carboxyl, alkylcarbonyl, arylcarbonyl, hydroxyalkyl, mercaptoalkyl, carboxyalkyl, carboxyaryl, alkylcarbonylalkyl, alkyl carbonyl aryl, aminoalkyl, alkylaminoalkyl, dialkylaminoalkyl, arylaminoalkyl, diarylaminoalkyl, alkylcarbonylamino, haloalkylcarbonylamino, and an NSAID moiety having NSAID activity, wherein the NSAID moiety is optionally substituted with one or more triphenylphosphinyl C$_1$-C$_{12}$ alkyl substituents, or R$^6$ and R$^7$ together form =O;

R[8], R[9], R[10], and R[11] are the same or different and are selected from the group consisting of hydrogen, halogen, hydroxyl, mercapto, cyano, isothiocyanato (—NCS), $C_{1-12}$ alkyl, $C_{2-12}$ alkenyl, $C_{3-8}$ cycloalkyl, $C_{3-8}$ heterocycloalkyl, $C_{6-30}$ aryl, $C_{1-12}$ alkoxy, $C_{1-12}$ alkylthio, amino, alkylamino, dialkylamino, arylamino, diarylamino, alkylsulfonyloxy, carboxyl, alkylcarbonyl, arylcarbonyl, hydroxyalkyl, mercaptoalkyl, carboxyalkyl, carboxyaryl, alkylcarbonylalkyl, alkylcarbonylaryl, aminoalkyl, alkylaminoalkyl, dialkylaminoalkyl, arylaminoalkyl, diarylaminoalkyl, alkylcarbonylamino, haloalkylcarbonylamino, and an NSAID moiety having NSAID activity, wherein the NSAID moiety is optionally substituted with one or more triphenylphosphinyl $C_1$-$C_{12}$ alkyl substituents;

optionally one of R[6] and R[7] and one of R[8] and R[9] can be absent such that a double bond joins the two carbon atoms to which the remaining one of R[6] and R[7] and the remaining one of R[8] and R[9] are attached; and n is 0 or 1;

with the condition that the compound of formula (I) contains at least one NSAID moiety having NSAID activity, wherein the NSAID moiety is optionally substituted with one or more triphenylphosphinyl $C_1$-$C_{12}$ alkyl substituents, and bonded thereto;

wherein said NSAID moiety is optionally bonded through a linking group;

and when R[1] is =O, the nitrogen atom linked to R[1] is positively charged;

or a pharmaceutically acceptable salt thereof or an enantiomer thereof.

In an embodiment of the compound of formula (I), when R[1] is OH or O., R[2]-R[5] are methyl, n=1, R[8]-R[11] are hydrogen, and one of R[6]-R[7] is hydrogen and other is an NSAID moiety, said NSAID moiety is not a moiety of aspirin, ibuprofen, naproxen, ketorolac, or flurbiprofen.

The compounds of formula (I) comprise at least one nitroxide moiety. In an embodiment of the invention, the nitroxide moiety may be, for example, a compound comprising N—O., or a precursor of a nitroxide moiety comprising N—OH, N=O, or N—OZ, wherein Z is selected from the group consisting of $C_{1-12}$ alkyl, $C_{2-12}$ alkenyl, $C_{3-8}$ cycloalkyl, $C_{3-8}$ heterocycloalkyl, and $C_{6-30}$ aryl. In an embodiment of the invention, the precursor of a nitroxide moiety may provide N—O. or a moiety comprising N—O. in vivo.

In accordance with an embodiment, R[1] in the compound of formula (I) is O.

In accordance with an embodiment of the invention, R[2], R[3], R[4], and R[5] in the compound of formula (I) are $C_{1-12}$ alkyl, for example, $C_{1-4}$ alkyl, particularly methyl.

In accordance with an embodiment, at least one of R[6] and R[7] in the compound of formula (I) is an NSAID moiety having NSAID activity, wherein the NSAID moiety is optionally substituted with one or more triphenylphosphinyl $C_1$-$C_{12}$ alkyl substituents. For example, at least one of R[6] and R[7] is an NSAID moiety having NSAID activity, wherein the NSAID moiety is optionally substituted with one or more triphenylphosphinyl $C_1$-$C_{12}$ alkyl substituents and the other of R[6] and R[7] is hydrogen.

In accordance with an embodiment, n=1.

In accordance with an embodiment, R[8], R[9], R[10], and R[11] in the compound of formula (I) are the same or different and each is selected from the group consisting of hydrogen, halogen, hydroxyl, and $C_{1-12}$ alkyl, particularly hydrogen.

In accordance with an embodiment, the compound of formula (I) contains at least two NSAID moieties, optionally substituted with one or more triphenylphosphinyl $C_1$-$C_{12}$ alkyl substituents, bonded thereto. In accordance with another embodiment, the compound of formula (I) contains at least three NSAID moieties, optionally substituted with one or more triphenylphosphinyl $C_1$-$C_{12}$ alkyl substituents, bonded thereto. The NSAID moiety may be any suitable NSAID moiety having NSAID activity. The NSAID moiety of the compounds of formula (I) may have NSAID activity that is the same as, less than, or greater than the NSAID activity of the parent NSAID. In accordance with an embodiment, the NSAID moiety is selected from the group consisting of salicylates, propionic acid derivatives, acetic acid derivatives, sulphonanilides, licofelone, enolic acid derivatives, fenamic acid derivatives, and selective COX-2 inhibitors. Specific examples of NSAID moieties include, but are not limited to, the NSAID selected from the group consisting of aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lomoxicam, isoxicam, mefenamic acid, meclofenamic acid, flufenamic acid, tolfenamic acid, celecoxicab, rofecoxib, valdecoxib, parecoxib, lumiracoxib, etoricoxib, nimesulide, and niflumic acid, and licofenac. In an embodiment of the invention, the NSAID moiety is not a moiety of aspirin, ibuprofen, naproxen, ketorolac, or flurbiprofen.

In an embodiment, the compound of formula (I) is

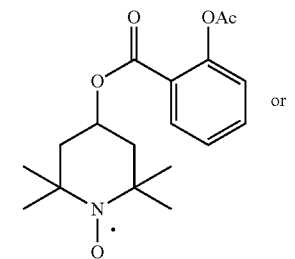

or

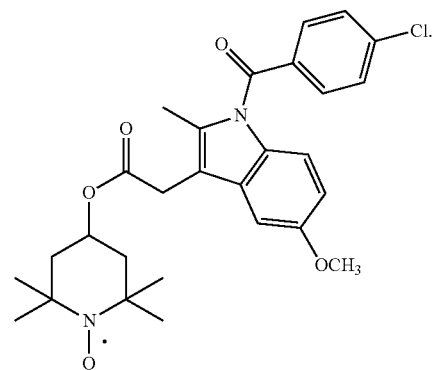

In an embodiment, the NSAID moiety or moieties are selected from the group consisting of:

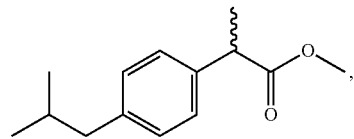

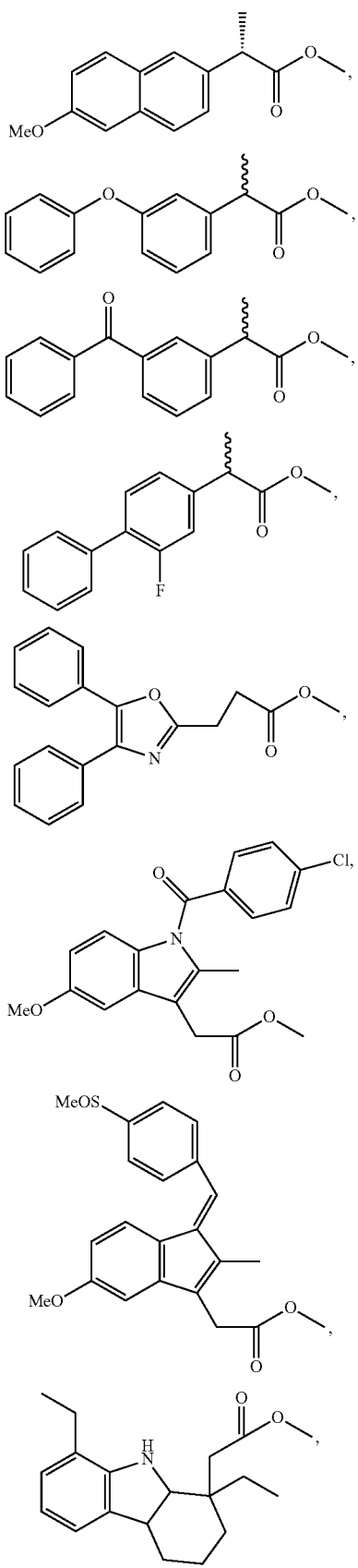
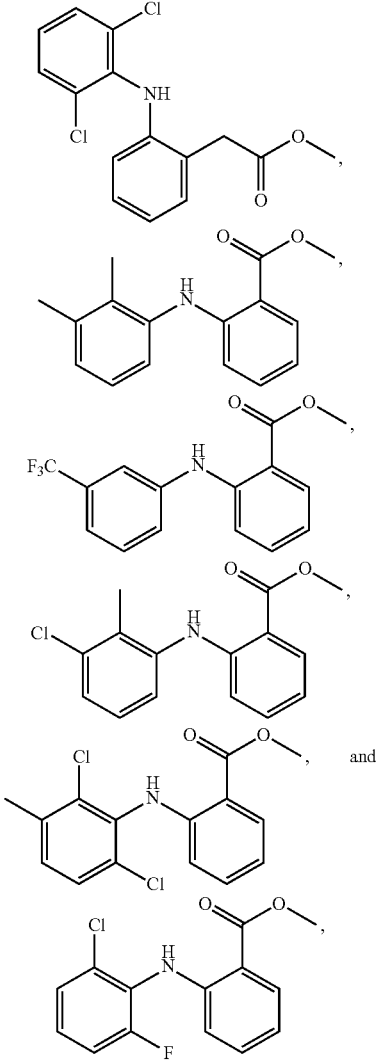
and any combinations thereof. In accordance with an embodiment, the NSAID moieties above are connected to the nitroxide moiety through the oxygen atom (—O—) of the carboxyl group.
In an embodiment, the NSAID moiety or moieties are selected from the group consisting of:
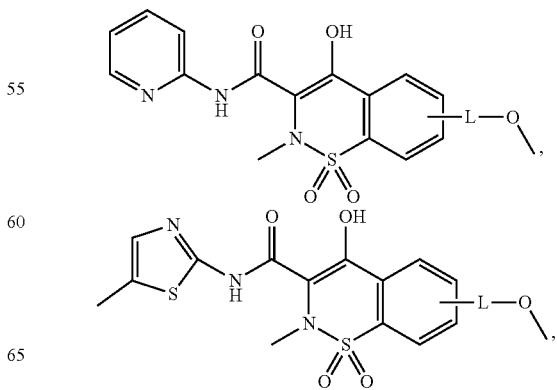

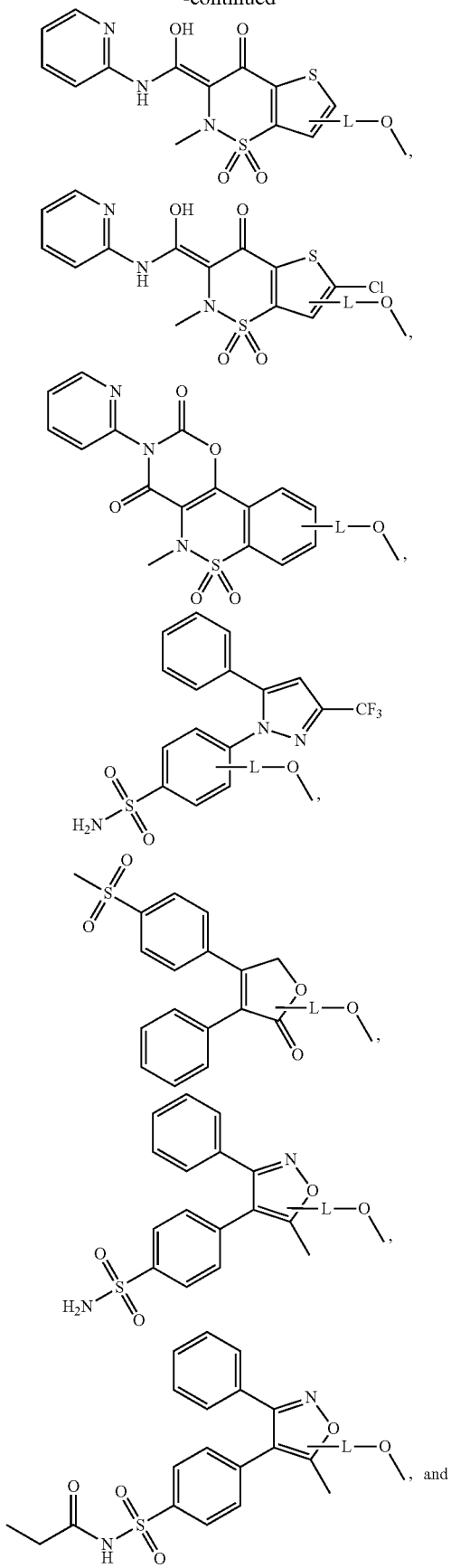

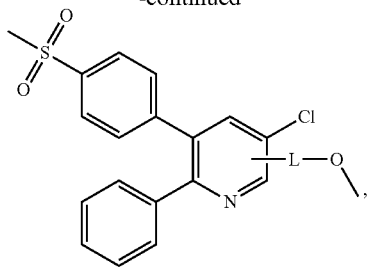

wherein L is a linking group selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted arylalkyl, carbonyl, thiocarbonyl, iminocarbonyl, carboxyl, and carbamoyl. In accordance with an embodiment, the NSAID moieties above are connected to the nitroxide moiety through the oxygen atom (—O—) of the carboxyl group.

In any of the embodiments above, the term "alkyl" implies a straight-chain or branched alkyl substituent containing from, for example, about 1 to about 12 carbon atoms, preferably from about 1 to about 8 carbon atoms, more preferably from about 1 to about 6 carbon atoms. In accordance with an embodiment, the alkyl group is preferably a $C_1$-$C_3$ alkyl. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs, such as in hydroxyalkyl, monohalo alkyl, dihalo alkyl, and trihalo alkyl.

In any of the embodiments above, the terms "hydroxyalkyl," "haloalkyl," and "aminoalkyl" refer to an alkyl group, as described herein, that has a hydroxyl, halo, or amino substituent, respectively. The substituent can be on any suitable carbon of the alkyl group (e.g., at the 1-, 2-, 3-, 4-, 5-, 6-, 7-, 8-, 9-, 10-, 11-, or 12-position).

In any of the embodiments above, the term "alkenyl," as used herein, means a linear or branched alkenyl substituent containing from, for example, about 2 to about 12 or about 3 to about 12 carbon atoms, preferably from about 3 to about 8 carbon atoms, more preferably from about 3 to about 6 carbon atoms. In accordance with an embodiment, the alkenyl group is preferably a $C_3$-$C_6$ alkenyl. Examples of alkenyl group include vinyl, allyl, 1-butenyl, 2-butenyl, 1-pentenyl, 2-pentenyl, 3-pentenyl, 1-hexenyl, and the like. A preferred alkenyl is allyl.

In any of the embodiments above, the term "alkynyl," as used herein, means an alkynyl substituent, linear or branched, containing at least one carbon-carbon triple bond and linear alkynyls contain from, for example, about 3 to about 12 carbon atoms (branched alkynyls are about 4 to about 12 carbons atoms), preferably from about 3 to about 8 carbon atoms (branched alkynyls are preferably from about 4 to about 8 carbon atoms), more preferably from about 3 to about 6 carbon atoms. Examples of such substituents include ethynyl, propynyl, propargyl, n-butynyl, pentynyl, isopentynyl, hexynyl, octynyl, dodecynyl, and the like.

In any of the embodiments above, the term "cycloalkyl," as used herein, means a monocyclic or bicyclic alkyl substituent containing from, for example, about 3 to about 8 carbon atoms, preferably from about 5 to about 8 carbon atoms, more preferably from about 5 to about 6 carbon atoms. Examples of such substituents include cyclopropyl, cyclobutyl, cyclopentyl, cyclohexyl, bicyclo[2.2.1]heptyl (e.g., (1s,4s)-bicyclo [2.2.1]heptyl), norbornyl, and the like.

In any of the embodiments above, the term "heterocycloalkyl," as used herein, means a stable, saturated, or partially unsaturated monocyclic, bicyclic, or spiro ring system containing 3 to 7 ring members of carbon atoms and other atoms selected from nitrogen, sulfur, and/or oxygen. Preferably, a heterocycloalkyl is a 5, 6, or 7-membered monocyclic ring and contains one, two, or three heteroatoms selected from nitrogen, oxygen, and/or sulfur. The heterocycloalkyl may be attached to the parent structure through a carbon atom or through any heteroatom of the heterocycloalkyl that results in a stable structure. Examples of heterocycloalkyl rings are thiazolinyl, imidazolidinyl, piperazinyl, homopiperazinyl, pyrrolyl, pyrrolinyl, pyrazolyl, pyranyl, piperidyl, and morpholinyl.

In any of the embodiments above, the term "aryl" refers to an unsubstituted or substituted aromatic carbocyclic moiety, as commonly understood in the art, and includes monocyclic, bicyclic, and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise $4n+2\pi$ electrons, according to Hückel's Rule, wherein $n=1, 2$, or 3.

In any of the embodiments above, the term "alkoxy" embraces a linear or branched alkyl group attached to a divalent oxygen. The alkyl group of alkoxy is as defined above. Examples of alkoxy groups include methoxy, ethoxy, n-propoxy, isopropoxy, n-butoxy, sec-butoxy, isobutoxy, tert-butoxy, n-pentoxy, isopentoxy, n-hexoxy, and the like. In accordance with an embodiment, the alkoxy group is preferably a $C_1$-$C_3$ alkoxy.

The term "alkylthio" refers to substituents in which linear or branched alkyl groups are attached to divalent sulfur. The alkyl group is as defined above.

In any of the embodiments above, the term "halo" refers to a halogen selected from the group consisting of fluorine, chlorine, bromine, and iodine, preferably chlorine or bromine.

In any of the embodiments above, the term "amino" refers to —$NH_2$. The term "alkylamino" refers to a secondary amine substituent with one hydrogen and one alkyl group directly attached to a trivalent nitrogen atom. The term "dialkylamino" refers to a tertiary amine substituent with two of the same or different $C_{1-12}$ alkyl groups directly attached to a trivalent nitrogen atom.

In any of the embodiments above, the term "carboxy" or "carboxyl" refers to the group —C(O)OH.

In any of the embodiments above, whenever a range of the number of atoms in a structure is indicated (e.g., a $C_{1-12}$, $C_{1-8}$, $C_{1-6}$, or $C_{1-4}$ etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

The compounds of the invention include stereoisomers, diastereoisomers, or mixtures thereof, e.g., racemic mixtures.

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

The compounds of the invention or a composition thereof can potentially be administered as a pharmaceutically acceptable acid-addition, base neutralized or addition salt, formed by reaction with inorganic acids, such as hydrochloric acid, hydrobromic acid, benzene sulfonic acid, methane sulfonic acid, toluene sulfonic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The invention also includes solvent addition forms ("solvates") of the compounds of the invention. Some compounds have a tendency to trap a fixed molar ratio of solvent molecules in the crystalline solid state, thus forming a solvate. When the compound of formula (I) is placed in a system in which a certain solvent is brought to a vapor form, in some situations, the compound, together with the molecules of the solvent, forms a crystal. The material formed by crystallization of the compound of formula (I) and the solvent in a three-dimensional order is called a solvate herein. The solvent can be associated with a crystalline solid form of a compound of formula (I) in various ways. The interaction can be due to weak binding (e.g., hydrogen bonding, van der Waals, and dipole-dipole) or by entrapment (e.g., liquid inclusion).

A solvate can be formed by a variety of methods, many of which are known in the art. A compound of formula (I) can be combined with one or more solvents by any suitable method (e.g., crystallization, lyophilization, film coating, spray drying, suspension, wetting, grinding, vapor sorption, etc.). For example, a compound of formula (I) can be combined with a particular solvent(s) and heated to boiling. The solution can then be slowly cooled to allow formation of the solvate crystals. Cooling can occur at room temperature or at a reduced temperature (e.g., an ice bath and/or refrigerated conditions). Controlling the temperature can be influential in the formation of solvates. Typically a lower temperature favors solvate formation. The formed solvate can be characterized by analytical methods such as thermogravimetric analysis (TGA), differential scanning calorimetry (DSC) alone or with infrared (IR) and/or mass spectrometry, x-ray powder diffraction, moisture sorption experiments, hot-stage polarized light microscopy, or a combination of these methods. Various techniques to prepare solvates are known in the art. See, e.g., J. Keith Guillory, "Generation of Polymorphs, Hydrates, and Solvates, and Amorphous Solids," *Drugs and the Pharmaceutical Sciences*, 95 (Polymorphism in Pharmaceutical Solids): 183-226 (1999); and Greisser, U., "The Importance of Solvates" in *Polymorphism*, Hilfiker, R., Ed., (Wiley-VCH Verlag GmbH & Co. KGaA: Weinheim, Germany, 2006), pages 211-233.

A solvate means a solvent addition form that contains either stoichiometric or non-stoichiometric amounts of solvent. A stoichiometric solvate implies a fixed, although not necessarily integral, ratio of solvent to compound (e.g., a solvent coordination number of 1, 2, 3, 4, 5, 6, etc.). A preferred solvent coordination number of a stoichiometric solvate is 1. A non-stoichiometric solvate can be an interstitial solid solution or an interstitial co-crystal. The solvent content of a solvate can be any suitable value, including a multiple of the molar compound ratio such that the solvent coordination number is a non-integral number (e.g., 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, etc.). The amount of solvent in the structure generally depends on the partial pressure of the solvent in the environment of the solid and the temperature (Greisser, U., "The Importance of Solvates" in *Polymorphism*, Hilfiker, R., Ed., (Wiley-VCH Verlag GmbH & Co. KGaA: Weinheim, Germany, 2006), pages 211-233).

The solvent can be any suitable solvent, i.e., the solvent is not particularly limited as long as a solvate of the compound of formula (I) can be formed. Solvents usable for solvate formation include water, alcohols, ethers, esters, alkanes, dichloromethane, chloroform, acetone, acetonitrile, toluene, tetrahydrofuran (THF), dimethylformamide (DMF), dimethyl sulfoxide (DMSO), dioxane, and combinations thereof. In some embodiments, the solvate contains a mixture of solvents, such as a combination of two or more of the aforementioned solvents. Preferably the solvent should have relatively low toxicity and can be removed from the compound of formula (I) to a level that is acceptable according to The International Committee on Harmonization (ICH) guidelines ("ICH Q3C Impurities: Guideline for Residual Solvents, International Conference on Harmonization of Technical Requirements for Registration of Pharmaceuticals for Human Use," Geneva, Switzerland, July 1997). Preferred solvents include water, alcohols, ethers, esters, and alkanes. If the solvent is water, the solvate formed is a "hydrate," whereas when the solvent is alcohol, the solvate formed is an "alcoholate." Specific examples of preferred solvents usable for solvate formation include water, $C_{1-4}$ alcohol (e.g., methanol, ethanol, propanol, isopropanol, and n-butanol), $C_{1-4}$ ether (e.g., diethyl ether), an ester of a $C_{1-6}$ (preferably $C_{1-4}$) alkyl acetate (e.g., methyl acetate, ethyl acetate, propyl acetate, and butyl acetate), a $C_{5-7}$ alkane (e.g., pentane, hexane, and heptane), and combinations thereof. Mixed solvates include, for example, water/ethanol, water/methanol, water/acetone, water/hexane, and water/DMF.

A compound of formula (I) or a salt or enantiomer thereof, can be prepared by the following exemplary method. An ester bond may be formed between a nitroxide moiety and an NSAID by a condensation reaction.

Without being bound to a particular theory or mechanism, it is contemplated that the compounds of formula (I) and salts and enantiomers thereof are capable of oxidizing superoxide ($O_2^-$). Accordingly, it is contemplated that the compounds of formula (I) and salts and enantiomers thereof may provide beneficial antioxidant effects such as, for example, protection against oxidative stress and the reduction of free radicals. It is also contemplated that the compounds of formula (I) and salts and enantiomers thereof may reduce or prevent thrombosis and/or gut toxicity.

The invention provides a pharmaceutical composition comprising (a) the compound of formula (I) or a salt or enantiomer thereof and (b) a pharmaceutically acceptable carrier. In the pharmaceutical compositions described herein, any suitable pharmaceutically acceptable carrier can be used, and such carriers are well known in the art. The choice of carrier will be determined, in part, by the particular site to which the pharmaceutical composition is to be administered and the particular method used to administer the pharmaceutical composition.

Suitable formulations include aqueous and non-aqueous solutions, isotonic sterile solutions, which can contain antioxidants, buffers, bacteriostats, and solutes that render the formulation isotonic with the blood or other bodily fluid of the intended recipient, and aqueous and non-aqueous sterile suspensions that can include suspending agents, solubilizers, thickening agents, stabilizers, and preservatives. In one embodiment, the pharmaceutically acceptable carrier is a liquid that contains a buffer and a salt. The formulation can be presented in unit-dose or multi-dose sealed containers, such as ampoules and vials, and can be stored in a freeze-dried (lyophilized) condition requiring only the addition of the sterile liquid carrier immediately prior to use. Extemporaneous solutions and suspensions can be prepared from sterile powders, granules, and tablets. In one embodiment, the pharmaceutically acceptable carrier is a buffered saline solution.

Further carriers include sustained-release preparations, such as semipermeable matrices of solid hydrophobic polymers containing the active agent, which matrices are in the form of shaped articles (e.g., films, liposomes, or microparticles). Alternatively, a delayed release formulation, including an enteric coating comprising a compound of formula (I) or a salt or enantiomer thereof, can be prepared.

The pharmaceutical composition can include carriers, thickeners, diluents, buffers, preservatives, surface active agents, and the like. The pharmaceutical compositions can also include one or more additional active ingredients, such as antimicrobial agents, anti-inflammatory agents, anesthetics, and the like.

The pharmaceutical composition comprising the compound of formula (I) or a salt or enantiomer thereof can be formulated for any suitable route of administration, depending on whether local or systemic treatment is desired, and on the area to be treated. The pharmaceutical composition can be formulated for parenteral administration, such as intravenous, intraperitoneal, intrathecal, intraarterial, subcutaneous, intramuscular, or intratumoral injection. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier immediately prior to use. Extemporaneous injection solutions and suspensions can be prepared from sterile powders, granules, and tablets of the kind previously described.

The pharmaceutical composition comprising the compound of formula (I) or a salt or enantiomer thereof can be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

The pharmaceutical composition also can be administered orally. Oral compositions can be in the form of powders or granules, suspensions or solutions in water and/or non-aqueous media, capsules, pills, sachets, or tablets. Thickeners, flavorings, diluents, emulsifiers, dispersing aids, or binders may be desirable.

If desired, tablets or pills can be coated with a sugar coating, or a gastric or enteric coating agent. The term "enteric coating" means a coating or barrier applied to a dosage form that can control the location in the digestive system where the compound of formula (I) or a salt or enantiomer thereof is absorbed. For example, an enteric coating can be used to protect the drug from the destructive action of the enzymes or low pH environment of the stomach. In certain embodiments, the enteric coated dosage form can be regarded as a type of delayed release dosage form. Enteric coatings work by presenting a surface that is substantially stable at acidic pH, but breaks down at higher pH to allow release of the drug in the intestine.

An enteric coating can comprise an enteric polymer, which is a polymeric substance that when used in an enteric coating, is substantially insoluble and/or substantially stable under acidic conditions exhibiting a pH of less than about 5 and which is substantially soluble or can decompose under conditions exhibiting a pH of about 5 or more. Non-limiting examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate and mixtures thereof. Enteric polymers can be used individually or in combination with other hydrophobic or hydrophilic polymers in an enteric coating. Enteric polymers can be combined with other pharmaceutically acceptable excipients to either facilitate processing of a coat comprising the enteric polymer or to alter the functionality of the coating.

Additionally, the compound of formula (I) or a salt or enantiomer thereof can be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable carriers and their formulations are further described in A. R. Gennaro, ed., *Remington: The Science and Practice of Pharmacy* (19th ed.), Mack Publishing Company, Easton, Pa. (1995).

The compound or a pharmaceutical composition comprising at least one compound of formula (I) or a salt or enantiomer thereof can be administered in or on a device that allows controlled or sustained release of the compound of formula (I) or a salt or enantiomer thereof, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the active agents. The pharmaceutical compositions of the inventive method also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid. Of course, administration of the compound or pharmaceutical composition can be accomplished via any route that efficiently delivers the active agents to the target tissue.

The inventive methods comprise administering an effective amount of a compound of formula (I) or a salt or enantiomer thereof. An "effective amount" means an amount sufficient to show a meaningful benefit in an individual, e.g., reducing the adverse effects of, treatment, healing, prevention, delay of onset, or amelioration of other relevant medical condition(s) associated with a particular disorder (e.g., a cardiovascular disorder). Preferably, one or more symptoms of the disorder are prevented, reduced, or eliminated subsequent to administration of a compound of formula (I) or a salt or enantiomer thereof, thereby effectively treating the disorder to at least some degree.

Effective amounts may vary depending upon the biological effect desired in the individual, condition to be treated, and/or the specific characteristics of the compound of formula (I) or a salt or enantiomer thereof, and the individual. In this respect, any suitable dose of the compound of formula (I) or a salt or enantiomer thereof can be administered to the patient (e.g., human), according to the type of disorder to be treated. Various general considerations taken into account in determining the "effective amount" are known to those of skill in the art and are described, e.g., in Gilman et al., eds., Goodman And Gilman's: *The Pharmacological Bases of Therapeutics*, 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or a salt or enantiomer thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I) or (II) comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

For purposes of the present invention, the term "patient" preferably is directed to a mammal. Mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The invention further provides a method of treating a disorder in a patient comprising administering an effective amount of a compound of formula (I) or a salt or enantiomer thereof, wherein the disorder is inflammation, cancer, diabetes, a cardiovascular disorder, weight gain, asthma, polyps, or chronic pain. Preferably, the disorder is cancer. Preferably, one or more symptoms of the disorder are prevented, reduced, or eliminated subsequent to administration of the compound of the invention, thereby effectively treating or preventing the disorder to at least some degree.

The cardiovascular disorder can be, for example, coronary artery disease, aneurysm, arteriosclerosis, atherosclerosis (including atherosclerotic plaque rupture and cardiac transplant atherosclerosis), myocardial infarction, hypertension, ischemia, embolism, stroke, thrombosis, thromboembolism, restenosis, angina, shock, or chronic or acute heart failure.

In an embodiment, the disorder is thrombosis. Thrombosis may include the formation of a blood clot in a blood vessel anywhere in the body of the animal. Thrombosis may include venous thrombosis (e.g., deep vein thrombosis, portal vein thrombosis, renal vein thrombosis, Budd-Chiari syndrome, jugular vein thrombosis, Paget-Schroetter disease, and cerebral venous sinus thrombosis) and/or arterial thrombosis.

Cancers treatable with the methods described herein include tumors associated with the oral cavity (e.g., the tongue and tissues of the mouth) and pharynx, the digestive system (e.g., the esophagus, stomach, small intestine, colon, rectum, anus, liver, gall bladder, and pancreas), the respiratory system (e.g., the larynx, lung, and bronchus), bones and joints (e.g., bony metastases), soft tissue, the skin (e.g., melanoma and squamous cell carcinoma), breast, the genital system (e.g., the uterine cervix, uterine corpus, ovary, vulva, vagina, prostate, testis, and penis), the urinary system (e.g., the urinary bladder, kidney, renal pelvis, and ureter), the eye and orbit, the brain and central nervous system (CNS) (e.g., glioma), and the endocrine system (e.g., thyroid). The target tissue also can be located in lymphatic or hematopoietic tissues. For example, the tumor can be associated with lymphoma (e.g., anaplastic large-cell lymphoma, Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). The tumor to be treated is not necessarily the primary tumor. Indeed, the tumor can be a metastasis of a primary tumor located in a different tissue or organ.

Specific examples of cancers treatable with the present methods include, without limitation, adrenocortical carcinoma, AIDS-related lymphoma, AIDS-related malignancies, anal cancer, cerebellar astrocytoma, bile duct cancer (e.g., extrahepatic bile duct cancer), bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, eye cancers, including intraocular melanoma, and retinoblastoma, gallbladder cancer, gastrointestinal carcinoid tumor, gastrointestinal stromal cancer, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/ plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell lymphoma, testicular cancer, malignant thymoma, thyroid cancer, gestational trophoblastic tumor, urethral cancer, uterine sarcoma, vaginal cancer, vulvar cancer, and Wilms' tumor. See, e.g., *Harrison's Principles of Internal Medicine*, Eugene Braunwald et al., eds., pp. 491-762 (15th ed. 2001). Preferably, the cancer is gastric cancer, colon cancer, lung cancer, or breast cancer.

Chronic pain can be caused by any underlying condition or disorder, such as neuropathic pain conditions, diabetic peripheral neuropathy, post-herpetic neuralgia, trigeminal neuralgia, post-stroke pain syndromes, or cluster or migraine headaches.

Inflammation can be acute inflammation or chronic inflammation. Inflammation can be, but is not necessarily, caused by or associated with any number of conditions, including asthma, an autoimmune disease (e.g., diabetes mellitus type 1), inflammatory bowel disease, pelvic inflammatory disease, reperfusion injury, rheumatoid arthritis, and vasculitis. The inflammation also can be coronary plaque inflammation, bacterial-induced inflammation (e.g., Chlamydia-induced inflammation), viral induced inflammation, or inflammation associated with surgical procedures (e.g., vascular grafting, coronary artery bypass surgery, and revascularization procedures (e.g., angioplasty, stent placement, endarterectomy, and vascular procedures involving arteries, veins, and capillaries)). The inflammation can also be eye inflammation (e.g., uveitis; conjunctivitis; eye inflammation due to allergic reaction, surgery, infection or trauma; ocular surface inflammation; lacrimal gland inflammation; blepharitis; and/or blepharoconjunctivitis). In an embodiment of the invention, when the disorder is eye inflammation, $R^1$ in formula (I) is selected from the group consisting of OZ, O., and =O.

Diabetes can include Type 1 diabetes, Type 2 diabetes, and/or gestational diabetes.

Weight gain can include obesity or weight gain in a patient such that the patient's weight exceeds a healthy weight as determined, e.g., by Body Mass Index (BMI).

In an embodiment, the invention provides a method of inducing weight loss in a patient comprising administering to the patient an effective amount of a compound of formula (I) or salt or enantiomer thereof.

Polyps may include benign, cancerous, or pre-cancerous polyps. An embodiment of the invention provides a method of treating polyps, preventing formation or growth of polyps, or preventing the progression of polyps into cancer in a patient comprising administering to the patient an effective amount of a compound of formula (I) or salt or enantiomer thereof.

An embodiment of the invention provides a compound of formula (I) or salt or enantiomer thereof for use in treating or preventing a disorder in an animal, wherein the disorder is inflammation, cancer, diabetes, a cardiovascular disorder, weight gain, asthma, polyps, or chronic pain.

An embodiment of the invention provides the use of a compound of foimula (I) or salt or enantiomer thereof in the manufacture of a medicament for treating or preventing a disorder in an animal, wherein the disorder is inflammation, cancer, diabetes, a cardiovascular disorder, weight gain, asthma, polyps, or chronic pain.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

The compounds of formula (I) and their salts and enantiomers, and fragments thereof, may comprise a nitroxide moiety, which has paramagnetic characteristics that can be examined using, e.g., electron paramagnetic resonance (EPR). In this regard, an embodiment of the invention further provides a method of imaging a cell, tissue, or organ in the body of an animal comprising administering a compound of formula (I) or salt or enantiomer thereof to the animal and detecting the compound, salt, enantiomer, or fragment thereof, in the body of the animal. Accordingly, the location and/or consumption of the compound of formula (I), salt, enantiomer, or fragment thereof in the body of the animal may be visualized and monitored using any suitable method, e.g., EPR, magnetic resonance imaging (MRI), or a combination thereof. For example, tumors may comprise free radicals, and the consumption of the compounds of formula (I) or salts or enantiomers thereof, which have antioxidant properties, by the tumor can be visualized and monitored. In an embodiment of the invention, consumption of the compounds of formula (I) or salts or enantiomers thereof, by the tumor can produce fragments of the compounds of formula (I) or salts or enantiomers thereof. The fragment may be any suitable fragment of the compounds of formula (I) or their salts or enantiomers including, but not limited to, a nitroxide moiety (e.g., TEMPO). Accordingly, in an embodiment, the tissue may be a tumor. In another embodiment, the cell may be an inflammatory cell.

The following examples further illustrate the invention but, of course, should not be construed as in any way limiting its scope.

EXAMPLE 1

This example demonstrates a method of synthesis of TEMPO-aspirin and TEMPO-indomethacin, compounds in accordance with an embodiment of the invention.

Dimethyl sulfoxide (DMSO); 1-(4,5-Dimethylthiazol-2-yl)-3,5-diphenylformazan (MTT); acetyl salicylic acid (ASA or aspirin); indomethacin (IND); and 2,2,6,6-Tetramethyl-1-piperidinyloxy (TEMPO) were purchased from Sigma-Aldrich (St. Louis, Mo., USA).

4-Hydroxy-TEMPO, indomethacin and O-acetylsalicyloyl chloride were purchased from Sigma Aldrich Chemical Company and used as received. Analytical thin layer chromatography (TLC) was performed on silica gel plates with QF-254 indicator. Visualization was accomplished with ultraviolet (UV) light, iodine, and phosphomolybdic acid. Solvents for extraction and purification were technical grade and used as received. All reactions were performed in flame-dried glassware under an inert atmosphere of dry argon.

$^1$H NMR and $^{13}$C NMR spectra were recorded in $CDCl_3$ using a Bruker Avance 300 MHz NMR spectrometer. Chemical shifts are given in ppm ($\delta$); multiplicities are indicated by s (singlet), d (doublet), t (triplet), q (quartet), m (multiplet), and b (broadened). Mass spectra were obtained on an Agilent Technologies 1100 LC/MSD Trap instrument.

TEMPO-ASA (1): Pyridine (0.45 mL, 5.50 mmol) was added to a solution of 4-hydroxy-TEMPO (0.86 g, 5.00 mmol), and acetylsalicyloyl chloride (1.09 g, 5.50 mmol) in $CH_2Cl_2$ (6 mL) at 0° C. The solution was stirred at room temperature overnight and the precipitate was removed by filtration. The filtrate was washed with water (6 mL), 10% aq. $NaHCO_3$ (10 mL), 2 M aq. HCl (10 mL), and water (6 mL). The $CH_2Cl_2$ was dried, filtered, concentrated, and purified by silica gel chromatography (7:3 hexanes:EtOAc, $R_f$=0.39) to give an orange oil (0.8 g, 48%). $^1$H NMR ($CDCl_3$ with 2 drops of TFA-d) 7.96 (d, 1H, J=7.0 Hz), 7.60 (t, 1H, J=7.1 Hz), 7.33 (d, 1H, J=7.5), 7.19 (d, 1H, J=7.5 Hz), 5.44 (bt, 1H, J=11.7 Hz), 2.37 (s, 3H), 2.42-2.00 (m, 4H), 1.54 (s, 6H), 1.46 (s, 6H); $^{13}$C NMR 169.8, 163.36, 150.96, 134.59, 131.66, 126.25, 123.98, 122.68, 67.37, 63.94, 41.74, 27.77, 20.7; MS: m/z, 335 [M+1]; Anal. Calcd. For $C_{18}H_{24}NO_5$: C, 64.65; H, 7.23; N, 4.19; Found: C, 64.73; H, 7.35; N, 4.20.

TEMPO-Indomethacin (2): Dicyclohexyl carbodiimide (DCC, 1.32 g, 6.4 mmol) was added to a solution of indomethacin (2.08 g, 5.8 mmol), 4-hydroxy-TEMPO (1 g, 5.8 mmol) and DMAP (0.16 g, 5.8 mmol) in $CH_2Cl_2$ (45 mL) at 0° C. The mixture was allowed to warm to room temperature (rt) and stirred overnight. The solvent was evaporated in vacuum and the residue was purified by silica gel chromatography (hexanes:EtOAc 7:3, $R_f$=0.36) to give an orange solid (2.3 g, 84%). $^1$H NMR ($CDCl_3$ with 2 drops of TFA-d) 7.69 (d, 2H, J=8.7 Hz), 7.55 (d, 2H, J=8.4 Hz), 6.8-7.4 (m, 3H), 5.32 (bt, 1H, J=11.4), 3.95 (s, 3H), 3.82 (s, 2H), 2.38 (s, 3H), 2.35-2.1 (m, 4H), 1.56 (s, 6H), 1.49 (s, 6H); $^{13}$C NMR 174.08, 172.13, 155.83, 141.34, 137.83, 132.81, 132.06, 130.18, 120.74, 116.97, 116.20, 113.41, 113.03, 109.42, 69.81, 66.18, 57.29, 41.65, 30.56, 28.14, 20.47, 13.60; MS: m/z 512 [M+]; Anal. Calcd. For $C_{28}H_{32}ClN_2O_5$: C, 65.68; H, 6.30, N, 5.47; Found: C, 66.28, H, 6.52, N, 5.38.

Scheme 1 below depicts the chemical synthesis of the ASA and indomethacin-nitroxide conjugates (1) and (2). Condensation of 4-hydroxy-TEMPO with acetylsalicyloyl chloride gave (1) in 48% yield and DCC-mediated coupling of 4-hydroxy-TEMPO with indomethacin gave (2) in 84% yield. The NMR spectroscopy, mass spectrometry and elemental analysis (set forth above) supported the structure of both 1 and 2.

Scheme 1

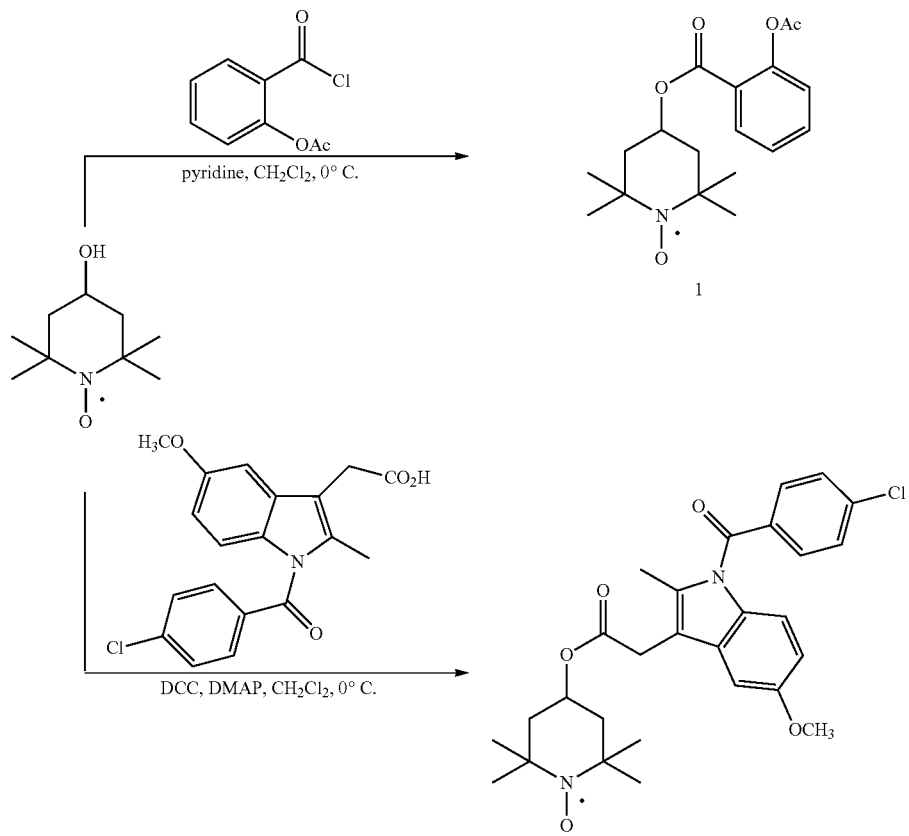

EXAMPLE 2

This example demonstrates some of the physical properties of TEMPO-aspirin and TEMPO-indomethacin, compounds in accordance with an embodiment of the invention.

Nitroxide modified NSAIDs may be characterized by different physical techniques such as electron paramagnetic resonance (EPR) and electrochemistry. Nitroxides, such as TEMPO, have paramagnetic characteristics that can be examined using EPR (Monti et al., *Free Radic Biol. Med.*, 21: 463-470 (1996)).

EPR measurements were performed in a gas permeable TEFLON capillary tube of 0.81 mm inner diameter, 0.38 mm wall thickness, and 15 cm length (Samuni et al., *Antioxid. Redox. Signal*, 6: 587-95 (2004)). The capillary tube was folded twice and inserted in a narrow quartz tube, then placed in the cavity of a Varian E-109 X-band spectrometer. The measurements were performed under aerobic conditions and at room temperature. The EPR parameters were: Field set at 3355 G, Scan Range $10\times10^1$ G, time constant: 0.128, Mod. Ampl. $0.5\times10^1$ H, RG: $8.0\times10^2$, 9.36 GHz microwave frequency, 100 kHz modulation frequency, and 10 mW microwave power.

The EPR spectra showed a triplet characteristic of this type of nitroxide in both ASA (1) and indomethacin (2) derivatives. These spectra demonstrated that the integrity of the nitroxide was preserved with the modification of the NSAID. Nitroxides have been shown to be reduced by cells, as indicated by loss of the triplet. Using this parameter, a single peak can be monitored to obtain kinetic information of cellular and biochemical reduction rates (Swartz et al., *Biochim Biophys Acta*, 888: 82-90 (1986)). In the presence of A549 cells (lung adenoma cell line), a rapid loss of the triplet was observed (monitored at 3360 G) indicating reduction of these compounds, on incubation with cells, with a half life ($t_{1/2}$) for TEMPO-indomethacin (compound 2) of ~24 min. and for TEMPO-aspirin (compound 1) of ~2.4 min. The comparable value for TEMPO was ~13 min. (FIG. 1). The different rates of reduction for these compounds were indicative of their rates of cellular uptake and intracellular reduction.

Nitroxides undergo one electron reduction and oxidation, which provides their antioxidant characteristics. Cyclic Voltammetry (CV) measurements of the nitroxide-NSAIDs were taken with an EG Potensiostat/Galvanostat Model 273A, from AMETEK Princeton Applied Research (Oak Ridge, Tenn.). Measurements were performed at room temperature in PBS or 50% organic solvents, using the platinum auxiliary electrode and Ag/AgCl (saturated KCl) reference electrode.

The cyclic voltammogram in PBS showed an oxidation potential for TEMPO-aspirin ($E_{ox}$=0.72V versus Ag/AgCl (or 0.83 vs NHE)), similar to that for TEMPO ($E_{ox}$=0.622 V vs. NHE, $E_{1/2}$=197 mV) or TEMPOL ($E_{ox}$=0.810 V vs. NHE) (Krishna et al., *Proc. Natl. Acad. Sci.*, 89:5537-41 (1992)). Due to the solubility of TEMPO-indomethacin, the cyclic voltametry was performed in acetonitrile. The cyclic voltammogram of TEMPO-indomethacin in acetonitrile (100 mM tetrabutylammonium chloride) ($E_{ox}$=1.312V versus Ag/AgCl) compared to TEMPO under the same conditions ($E_{ox}$=1.0 V vs. NHE). The cyclic voltammographs of both TEMPO-aspirin and TEMPO-indomethacin were reversible, indicating stable one electron oxidation, comparable to that of the parent nitroxides. These electron paramagnetic resonance and electrochemistry results suggested that both TEMPO-indomethacin and TEMPO-aspirin behave as characteristic nitroxides.

EXAMPLE 3

This example demonstrates that TEMPO-aspirin and TEMPO-indomethacin scavenge superoxide.

Nitroxides have the capability to mimic superoxide dismutase (SOD), thereby scavenging superoxide (Krishna et al., *J. Biol. Chem.*, 271: 26026-31 (1996)). The similarity of the electrochemical behavior of TEMPO-indomethacin and TEMPO-aspirin to that of TEMPO in Example 2 suggested that these might be capable of oxidizing $O_2^-$.

Superoxide was generated from the reaction of hypoxanthine (500 µM) with xanthine oxidase (10 mU) in PBS (pH 7.4, 25° C.) containing the metal chelator diethylenetriaminepentaacetic acid (DTPA, 50 µM). The rate of superoxide formation was assessed by ferricytochrome c (cyt c) (60 µM) reduction (550 nm, $\epsilon$=21,000 $M^{-1}$ $cm^{-1}$), as previously described (Wasserman et al., *Biochim. Biophys. Acta*, 623: 457-60 (1980)). Different drug doses (5-100 µM) were used to scavenge superoxide by the modified nitroxide-NSAIDs. Increasing concentration of TEMPO, TEMPO-aspirin, or TEMPO-indomethacin decreased the reduction rate of ferricytochrome c in a manner characteristic of the competition for superoxide. The solubility of these compounds limited the use of higher doses (>200 µM) in aqueous solutions for this test. The $IC_{50}$ for TEMPO was ~50 µM and the $IC_{50}$ for each of the modified compounds (1) and (2) was 100 µM, which suggested that the reduction rate was two times slower with respect to compound (1) (TEMPO-aspirin) or compound (2) (TEMPO-indomethacin) as compared to that of TEMPO (FIG. 2). The rate constant of these compounds were calculated from the typical plot shown on FIG. 5. A rate of $1.00\times10^4\pm0.06$ $M^{-1}$ $s^{-1}$ and $1.04\times10^4\pm0.08$ $M^{-1}$ $s^{-1}$ was obtained for compound (1) and (2) respectively. Previous reports at pH 7.4 show a rate of $1.2\times10^5$ $M^{-1}$ $s^{-1}$ for TEMPO and $6.5\times10^4$ $M^{-1}$ $s^{-1}$ for TEMPOL (Samuni et al., *Free Rad. Res. Comms.*, 9: 241-49 (1990); Krishna et al., *Proc. Natl. Acad. Sci.* 89: 5537-41 (1992)). These findings showed that nitroxide-modified NSAIDs can scavenge superoxide.

EXAMPLE 4

This example demonstrates inhibition of prostaglandin 2 ($PGE_2$) and leukotriene $B_4$ ($LTB_4$) production by TEMPO-aspirin and TEMPO-indomethacin, compounds in accordance with an embodiment of the invention.

The arachidonic acid pathway is the preferential target for NSAIDs (Yoshimura et al., *J. Biomed. Biotechnol.*, 467-89 (2009)). Here, the effectiveness of the nitroxide-NSAIDs against inhibiting the synthesis of eicosanoids was evaluated.

The A549 cell line was grown in Dulbecco's Modified Eagle Medium (DMEM) also supplemented with 10% heat inactivated fetal bovine serum and penicillin-streptomycin. The cells were maintained at 37 C in an atmosphere of 95% room air and 5% $CO_2$. The media was changed twice a week.

$PGE_2$ was measured by enzyme enzyme-linked immunosorbent assay (ELISA) (Cayman Chemical, Ann Arbor, Mich.). (1) or (2) was dissolved in DMSO at a concentration of 10 mg $ml^{-1}$ for the in vitro experiments. A549 cells in 24 well plates were treated with the compound for 30 min., then arachidonic acid (20 µg $ml^{-1}$) was added at 37° C. for 5 min. The samples were frozen at −80° C. until assayed for PGE2. A 100 µl sample was added to EIA buffer (900 µl). Diluted sample (25 µl) was then added to a 96 well plate. The samples were incubated overnight at 4° C. The plate was then washed 5 times (200 µA) and Edman's reagent was added. The absorbance at 450 nm was determined in an ELISA reader. The results are shown in Tables 1A-1B. Tables 1A-1B show the mean value±S.D. of 3 determinations. Percents were obtained using the formula: %: sample pg/ml/control pg/ml×100.

TABLE 1A

| Dose | PGE-2 | | | | | |
|---|---|---|---|---|---|---|
| | (1) | | | (2) | | |
| (μg ml$^{-1}$) | % | (pg ml$^{-1}$) | μM | % | (pg ml$^{-1}$) | μM |
| 0 | 100 | (282 ± 32) | 0 | 100 | (282 ± 32) | 0 |
| 1 | 82 | (230 ± 10)* | 3 | 78 | (220 ± 30)* | 2 |
| 3 | 81 | (227 ± 2)* | 9 | 66 | (187 ± 37)* | 6 |
| 10 | 71 | (200 ± 10)* | 30 | 49 | (140 ± 40)* | 20 |
| 30 | 50 | (142 ± 32)* | 90 | 36 | (102 ± 22)* | 60 |
| 100 | 29 | (82 ± 8)* | 300 | 27 | (77 ± 2)* | 200 |

TABLE 1B

| Dose | PGE-2 | | | | | | | | |
|---|---|---|---|---|---|---|---|---|---|
| | ASA | | | IND | | | TEMPO | | |
| (μg ml$^{-1}$) | % | (pg ml$^{-1}$) | μM | % | (pg ml$^{-1}$) | μM | % | (pg ml$^{-1}$) | μM |
| 0 | 100 | (42 ± 3) | 0 | 100 | (42 ± 3) | 0 | 100 | (42 ± 3) | 0 |
| 10 | 107 | (45 ± 7) | 55 | 50 | (21 ± 3)** | 28 | 133 | (56 ± 10) | 64 |
| 100 | 23 | (10 ± 2)** | 555 | 12 | (5 ± 1)** | 280 | 123 | (52 ± 8) | 640 |

When the A549 cells were treated with TEMPO-aspirin, the IC$_{50}$ of PGE2 production was 30 μg ml$^{-1}$ (90 μM). When the A549 cells were treated with TEMPO-indomethacin, the IC$_{50}$ of PGE2 production was 10 μg ml$^{-1}$ (19 μM) (Table 1A; *P<0.05, t-test). COX-2 inhibition was also intact (Table 1B; **P<0.001, t-test).

Several recent modified NSAIDs target both prostaglandin as well as leukotriene (Martel-Pelletier et al., *Ann. Rheum. Dis.*, 62:501-09 (2003)). Since nitroxides inhibit lipoxygenase (Rachmilewitz et al., *Gut*, 35: 1181-88 (1994)), the inhibition of LTB$_4$ in A549 cells by these compounds was evaluated. Leukotriene B4 from A549 cells treated as described above was examined using an ELISA assay kit (Cayman Chemical, Ann Arbor, Mich.; Cat No. 520111) according to the manufacturer's instructions. The results are shown in Tables 2A-2B. Tables 2A-2B show the mean value±S.D. of 3 determinations. Percents were obtained using the formula: %: sample pg/ml/control pg/ml×100.

TABLE 2A

| Dose | LTB4 | | | | | |
|---|---|---|---|---|---|---|
| | (1) | | | (2) | | |
| (μg ml$^{-1}$) | % | (pg ml$^{-1}$) | μM | % | (pg ml$^{-1}$) | μM |
| 0 | 100 | (46.61 ± 0.29) | 0 | 100 | (46.61 ± 0.29) | 0 |
| 0.01 | 98 | (45.86 ± 0.30) | 0.03 | 96 | (44.53 ± 0.30)* | 0.02 |
| 0.10 | 95 | (44.17 ± 0.30)* | 0.30 | 76 | (35.36 ± 0.30)* | 0.20 |
| 1.00 | 91 | (42.54 ± 0.29)* | 3.00 | 66.5 | (31.03 ± 0.29)* | 2.00 |
| 10.0 | 51 | (23.59 ± 0.32)* | 30.00 | 62.8 | (29.27 ± 0.29)* | 20.00 |

TABLE 2B

| Dose | LTB4 | | | | | | | | |
|---|---|---|---|---|---|---|---|---|---|
| | ASA | | | IND | | | TEMPO | | |
| (μg ml$^{-1}$) | % | (pg ml$^{-1}$) | μM | % | (pg ml$^{-1}$) | μM | % | (pg ml$^{-1}$) | μM |
| 0 | 100 | (100 ± 1) | 0 | 100 | (100 ± 1) | 0 | 100 | (100 ± 1) | 0 |
| 10 | 64 | (64 ± 13) | 55 | 100 | (100 ± 10) | 28 | 100 | (100 ± 2) | 64 |
| 100 | 62 | (62 ± 5) | 555 | 82 | (82 ± 9) | 250 | 100 | (100 ± 1) | 640 |

As shown in Table 2A, both TEMPO-aspirin and TEMPO-indomethacin blocked LTB$_4$ formation, with IC$_{50}$ values of ~30 μM for TEMPO-aspirin and ~20 μM for TEMPO-indomethacin. However, no inhibition was observed for the parent compounds (aspirin, indomethacin, TEMPO) at 10 μg ml$^{-1}$ or even at higher concentrations (100 μg ml$^{-1}$) (Table 2B). These results indicated that the modified nitroxides inhibited COX-2 and lipoxygenase 5 (5-LO) in A549 cells.

EXAMPLE 5

This example demonstrates that TEMPO-aspirin and TEMPO-indomethacin have anti-proliferative properties for lung adenoma cells.

NSAIDs have been used to induce cytotoxicity and reduce proliferation in lung tumor cells (Choy et al. *J. Natl. Cancer Inst.*, 95: 1440-52 (2003); Liao et al. *Clin. Cancer Res.* 11: 3342-48 (2005)). To assess the effectiveness and toxicity of these compounds in cancer cells, two assays were used: 1) proliferation assay 1-(4,5-Dimethylthiazol-2-yl)-3,5-diphenylformazan (MTT) and 2) a clonogenic assay.

Cell viability was determined using a standard colorimetric MTT assay. The cells were grown for 24 h in a 96-well cultured plate with a cell density of $5.0 \times 10^3$ cells/well with 100 μL of media. The cells were treated with different concentrations of individual compounds (0-300 μM) or the respective controls for 24 h. Then 10 μL of MTT (Sigma-Aldrich, St. Louis Mo.) was added to the culture media (5 mg $ml^{-1}$, PBS) and incubated at 37° C. for 3 h. The culture medium was decanted and 100 μL of DMSO was added to each well to dissolve the formazan crystals. After 5 min of agitation at 37° C., the absorbance was measured at 590 nm using a Perkin Elmer HTS 7000 Bio Assay Reader. GraphPad Prism software was used to determine P values by T-test analysis.

As shown in FIG. 3, proliferation was inhibited by TEMPO-indomethacin or TEMPO-aspirin but not by the parent compounds TEMPO, ASA, or indomethacin alone. These data indicated that the combination of nitroxide and NSAID had a greater affect on proliferation than the parent compound alone.

A standard clonogenic assay was performed to assess cell survival. A549 cells were trypsinized and plated ($1 \times 10^6$ cell/dish) in 60 $cm^2$ cultured dishes. The cells were incubated for 24 h and then treated with 30, 100, and 300 μM of TEMPO, (1), (2), or control for 24 h. After treatment, the cells were washed with PBS, trypsinized, counted, and then plated for colony formation. For each drug dose, the cells were plated in triplicates and incubated at 37° C. for 14 days. The colonies were stained with crystal violet and counted. T-test analysis of the data was performed using GraphPad Prism software for the determination of P values.

As shown in FIG. 4, cells exposed to TEMPO-indomethacin or TEMPO-aspirin demonstrated an increase in cell death as compared to the parent compounds. Both the cell viability and proliferation assays suggested that the nitroxide-NSAIDs have anti-proliferative properties for lung adenoma cells.

EXAMPLE 6

This example demonstrates that TEMPO-indomethacin has greater anti-inflammatory activity and lower gut toxicity as compared to indomethacin.

All animal experiments were carried out in compliance with the *Guide for the Care and Use of Laboratory Animal Resources* (National Research Council, 1996) and were approved by the National Cancer Institute Animal Care and Use Committee. Female athymic nude mice were supplied at 6 weeks of age by the Frederick Cancer Research Center and were housed five per cage in a climate-controlled environment. The compounds (1), (2), ASA, and indomethacin were prepared in DMSO while TEMPO was prepared in 5% DMSO/PBS pH 7.4. Each animal was weighed individually on the same day as the intraperitoneal (IP) injection. Different dosages were used to determine the maximum tolerated dose to be given to the animals. Each animal was monitored for up to 24 h and death was the end point of the experiment.

Table 3 summarizes the maximum tolerable dose for these drugs when injected IP into nude mice.

TABLE 3

| Compound | Molecular Weight (g $mol^{-1}$) | Maximum Tolerated Dose (MTD) (mg $kg^{-1}$) |
| --- | --- | --- |
| TEMPO | 156.25 | 140 |
| ASA | 180.15 | 100 |
| (1) | 334.39 | 50-100 |
| IND | 357.30 | 5 |
| (2) | 512.02 | 40 |

As shown in Table 3, TEMPO demonstrated a tolerance of 140 mg $kg^{-1}$ which is similar to other nitroxides such as TEMPOL (275 mg $kg^{-1}$) (Hahn et al., *Cancer Res.*, 52:1750-53 (1992)). The toxicity of compound (1) was similar to ASA, however compound (2) had an 8 fold (40 mg $kg^{-1}$) decrease in toxicity compared to the parent compound indomethacin (5 mg $kg^{-1}$).

Both subsequent anti-inflammatory and ulcerogenesis assays performed with TEMPO-indomethacin confirmed this improvement of the indomethacin derivate. The in vivo anti-inflammatory activity was evaluated using the carrageenan-induced foot paw edema model reported previously (Winter et al. *Proc. Soc. Exp. Biol. Med.*, 111: 544-47 (1962)).

As shown in Table 4, the anti-inflammatory assay showed that TEMPO-indomethacin was about 15% more potent ($ED_{50}=3.18$ mg $kg^{-1}$) than indomethacin ($ED_{50}=4.2$ mg $kg^{-1}$), which is an improvement considering that indomethacin is one of the most potent NSAIDs in the market.

TABLE 4

| Compound | Anti-inflammatory * $ED_{50}$ mg $kg^{-1}$ | UI |
| --- | --- | --- |
| IND | 4.2 | 34.1 |
| (2) | 3.18 | 3.6 |

* AI: The results are expressed as the effective dose of the test compound necessary to decrease by 50% the inflammatory response in the group of animals (n) 4.

Based on this, the potential ulcerogenic side-effects of TEMPO-indomethacin were evaluated using an acute model in rats. The ulcerogenesis assay was carried out following procedures reported previously (Winter et al. *Proc. Soc. Exp. Biol. Med.*, 111: 544-47 (1962); Velazquez et al., *J. Med. Chem.*, 48: 4061-67 (2005)). Compound (2) (30 mg $kg^{-1}$) and indomethacin (30 mg $kg^{-1}$) were suspended and administered P.O. in 1.2 mL of 1% methylcellulose solution. Animals were fasted for 24 h prior to compound administration. Six hours after administering the compound, the rats were euthanized, and their stomachs were removed and kept on ice. A magnifying lens was used to determine the number and length of the ulcers observed in each stomach. Each gastric lesion was measured along its greatest length in mm. The "ulcer index" (UI) for each test compound was calculated by adding the total length in mm of the individual ulcers in each stomach, divided by the number of animals in each group.

As shown in Table 4, the chemical modification of indomethacin with an anti-oxidant moiety (TEMPO) significantly reduced the ulcer index for TEMPO-indomethacin (UI=3.6) almost ten-fold, as compared to that of the parent drug indomethacin (UI=34.4). These results demonstrated that the addition of the anti-oxidant moiety TEMPO to the parent indomethacin not only improved the anti-inflammatory activity of TEMPO-indomethacin but also decreased the gut toxicity as compared with the parent compound.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

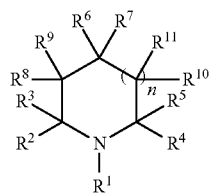

(I)

wherein $R^1$ is O.;

$R^2$, $R^3$, $R^4$, and $R^5$ are the same or different and are selected from the group consisting of hydrogen, $C_{1-12}$ alkyl, $C_{2-12}$ alkenyl, and $C_{2-12}$ alkynyl;

$R^6$ and $R^7$ are the same or different and are selected from the group consisting of hydrogen, halogen, hydroxyl, mercapto, cyano, isothiocyanato (—NCS), $C_{1-12}$ alkyl, $C_{2-12}$ alkenyl, $C_{3-8}$ cycloalkyl, $C_{3-8}$ heterocycloalkyl, $C_{6-30}$ aryl, $C_{1-12}$ alkoxy, $C_{1-12}$ alkylthio, amino, alkylamino, dialkylamino, arylamino, diarylamino, alkylsulfonyloxy, carboxyl, alkylcarbonyl, arylcarbonyl, hydroxyalkyl, mercaptoalkyl, carboxyalkyl, carboxyaryl, alkylcarbonylalkyl, alkylcarbonylaryl, aminoalkyl, alkylaminoalkyl, dialkylaminoalkyl, arylaminoalkyl, diarylaminoalkyl, alkylcarbonylamino, haloalkylcarbonylamino, and an NSAID moiety having NSAID activity, wherein the NSAID moiety is optionally substituted with one or more triphenylphosphinyl $C_1$-$C_{12}$ alkyl substituents; or $R^6$ and $R^7$ together form =O;

$R^8$, $R^9$, $R^{10}$, and $R^{11}$ are the same or different and are selected from the group consisting of hydrogen, halogen, hydroxyl, mercapto, cyano, isothiocyanato (—NCS), $C_{1-12}$ alkyl, $C_{2-12}$ alkenyl, $C_{3-8}$ cycloalkyl, $C_{3-8}$ heterocycloalkyl, $C_{6-30}$ aryl, $C_{1-12}$ alkoxy, $C_{1-12}$ alkylthio, amino, alkylamino, dialkylamino, arylamino, diarylamino, alkylsulfonyloxy, carboxyl, alkylcarbonyl, arylcarbonyl, hydroxyalkyl, mercaptoalkyl, carboxyalkyl, carboxyaryl, alkylcarbonylalkyl, alkylcarbonylaryl, aminoalkyl, alkylaminoalkyl, dialkylaminoalkyl, arylaminoalkyl, diarylaminoalkyl, alkylcarbonylamino, haloalkylcarbonylamino, and an NSAID moiety having NSAID activity, wherein the NSAID moiety is optionally substituted with one or more triphenylphosphinyl $C_1$-$C_{12}$ alkyl substituents;

optionally one of $R^6$ and $R^7$ and one of $R^8$ and $R^9$ can be absent such that a double bond joins the two carbon atoms to which the remaining one of $R^6$ and $R^7$ and the remaining one of $R^8$ and $R^9$ are attached; and n is 0 or 1;

with the condition that the compound of formula (I) contains at least two NSAID moieties, each optionally substituted with one or more triphenylphosphinyl $C_1$-$C_{12}$ alkyl substituents, bonded thereto;

wherein the NSAID moieties are each optionally bonded through a linking group;

or a pharmaceutically acceptable salt thereof or an enantiomer thereof, wherein the NSAID of the NSAID moieties is selected from the group consisting of fenoprofen, ketoprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, nimesulide, niflumic acid, and licofenac.

2. The compound, salt, or enantiomer of claim 1, wherein the compound contains at least three NSAID moieties, each optionally substituted with one or more triphenylphosphinyl $C_1$-$C_{12}$ alkyl substituents, bonded thereto.

3. The compound, salt, or enantiomer of claim 1, wherein the NSAID moieties are selected from the group consisting of:

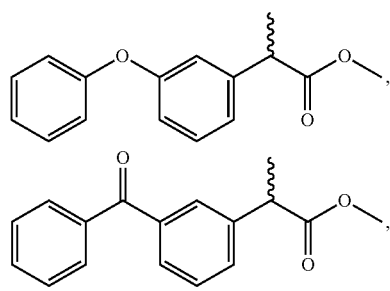

29
-continued

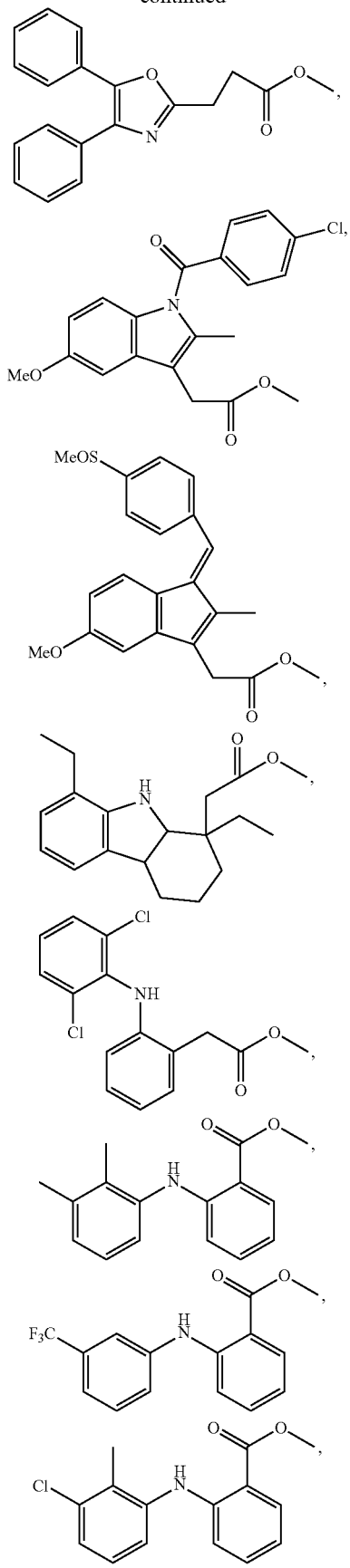

30
-continued

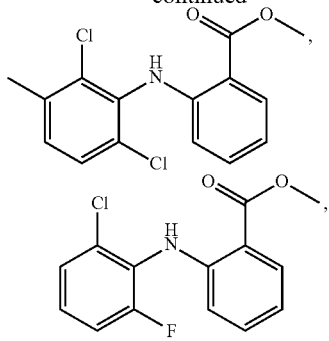

and

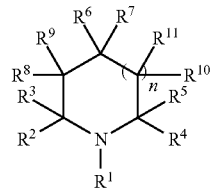

and any combinations thereof.

4. A compound of formula (I):

$$\text{(I)}$$

wherein
R$^1$ is O.;
R$^2$, R$^3$, R$^4$, and R$^5$ are the same or different and are selected from the group consisting of hydrogen, C$_{1-12}$ alkyl, C$_{2-12}$ alkenyl, and C$_{2-12}$ alkynyl;
R$^6$ and R$^7$ are the same or different and are selected from the group consisting of hydrogen, halogen, hydroxyl, mercapto, cyano, isothiocyanato (—NCS), C$_{1-12}$ alkyl, C$_{2-12}$ alkenyl, C$_{3-8}$ cycloalkyl, C$_{3-8}$ heterocycloalkyl, C$_{6-30}$ aryl, C$_{1-12}$ alkoxy, C$_{1-12}$ alkylthio, amino, alkylamino, dialkylamino, arylamino, diarylamino, alkylsulfonyloxy, carboxyl, alkylcarbonyl, arylcarbonyl, hydroxyalkyl, mercaptoalkyl, carboxyalkyl, carboxyaryl, alkylcarbonylalkyl, alkylcarbonylaryl, aminoalkyl, alkylaminoalkyl, dialkylaminoalkyl, arylaminoalkyl, diarylaminoalkyl, alkylcarbonylamino, haloalkylcarbonylamino, and an NSAID moiety having NSAID activity, wherein the NSAID moiety is optionally substituted with one or more triphenylphosphinyl C$_1$-C$_{12}$ alkyl substituents; or R$^6$ and R$^7$ together form =O;
R$^8$, R$^9$, R$^{10}$, and R$^{11}$ are the same or different and are selected from the group consisting of hydrogen, halogen, hydroxyl, mercapto, cyano, isothiocyanato (—NCS), C$_{1-12}$ alkyl, C$_{2-12}$ alkenyl, C$_{3-8}$ cycloalkyl, C$_{3-8}$ heterocycloalkyl, C$_{6-30}$ aryl, C$_{1-12}$ alkoxy, C$_{1-12}$ alkylthio, amino, alkylamino, dialkylamino, arylamino, diarylamino, alkylsulfonyloxy, carboxyl, alkylcarbonyl, arylcarbonyl, hydroxyalkyl, mercaptoalkyl, carboxyalkyl, carboxyaryl, alkylcarbonylalkyl, alkylcarbonylaryl, aminoalkyl, alkylaminoalkyl, dialkylaminoalkyl, arylaminoalkyl, diarylaminoalkyl, alkylcarbonylamino, haloalkylcarbonylamino, and an NSAID moiety having NSAID activity, wherein the NSAID moiety is optionally substituted with one or more triphenylphosphinyl C$_1$-C$_{12}$ alkyl substituents;

optionally one of $R^6$ and $R^7$ and one of $R^8$ and $R^9$ can be absent such that a double bond joins the two carbon atoms to which the remaining one of $R^6$ and $R^7$ and the remaining one of $R^8$ and $R^9$ are attached; and n is 0 or 1;

with the condition that the compound of formula (I) contains at least one NSAID moiety having NSAID activity, wherein the NSAID moiety is optionally substituted with one or more triphenylphosphinyl $C_1$-$C_{12}$ alkyl substituents, and bonded thereto;

or a pharmaceutically acceptable salt thereof or an enantiomer thereof;

wherein the NSAID moiety or moieties are selected from the group consisting of:

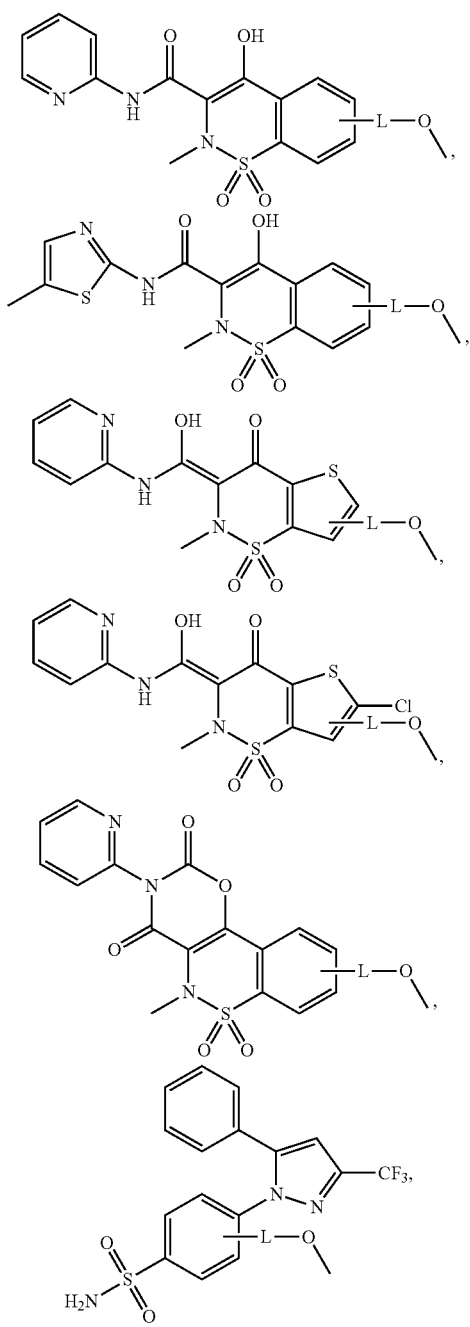

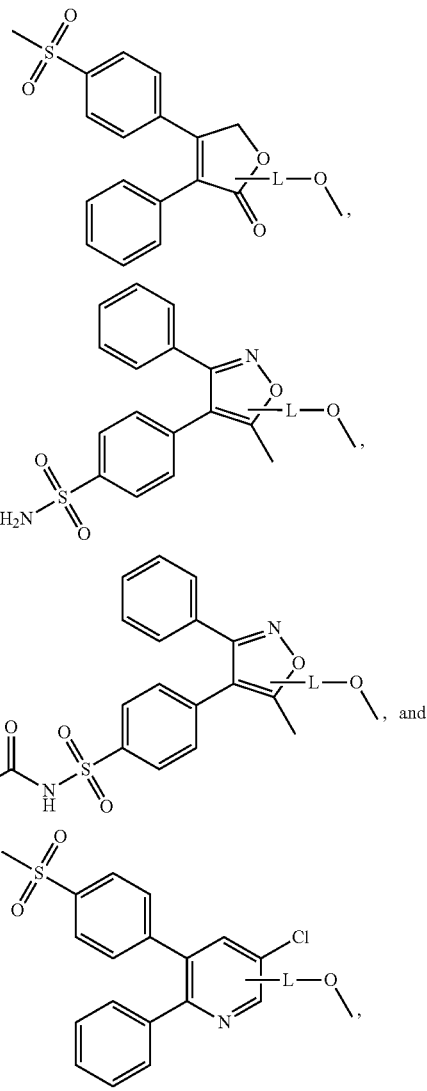

wherein L is a linking group selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted arylalkyl, carbonyl, thiocarbonyl, iminocarbonyl, carboxyl, and carbamoyl.

5. A pharmaceutical composition comprising a compound, salt, or enantiomer of claim 1 and a pharmaceutically acceptable carrier.

6. A pharmaceutical composition comprising a compound, salt, or enantiomer of claim 2 and a pharmaceutically acceptable carrier.

7. A pharmaceutical composition comprising a compound, salt, or enantiomer of claim 3 and a pharmaceutically acceptable carrier.

8. A pharmaceutical composition comprising a compound, salt, or enantiomer of claim 4 and a pharmaceutically acceptable carrier.

* * * * *